US00PP37609P2

(12) United States Plant Patent
Barends

(10) Patent No.: US PP37,609 P2
(45) Date of Patent: Aug. 18, 2026

(54) ***OSTEOSPERMUM* PLANT NAMED 'Doostmardarpup'**

(50) Latin Name: *Osteospermum ecklonis*
Varietal Denomination: Doostmardarpup

(71) Applicant: DUMMEN GROUP B.V., De Lier (NL)

(72) Inventor: Eveline Barends, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/418,845

(22) Filed: Dec. 12, 2025

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Osteospermum* plant named 'Doostmardarpup', characterized by its compact, broadly upright, uniform and mounding plant habit; moderately vigorous growth habit; freely and uniformly branching habit; freely and early flowering habit; and large single-type inflorescences with dark purplish red-colored ray florets.

1 Drawing Sheet

Botanical designation: *Osteospermum ecklonis.*
Cultivar denomination: 'DOOSTMARDARPUP'.

CROSS-REFERENCED TO RELATED APPLICATION

A European Community Plant Breeder's Rights application for the instant plant was filed by the Applicant/Assignee, Dümmen Group B.V. of De Lier, The Netherlands on Oct. 21, 2024, application No. 2024/2442 and published on Dec. 15, 2024. Foreign priority is not claimed to this application.

BACKGROUND OF THE INVENTION

The present invention relates to a new and distinct cultivar of *Osteospermum* plant, botanically known as *Osteospermum ecklonis*, and hereinafter referred to by the name 'Doostmardarpup'.

The new *Osteospermum* plant is a product of a planned breeding program conducted by the Inventor in Puerto Lumbreras, Spain and De Lier, The Netherlands. The objective of the program is to create and develop new compact *Osteospermum* plants that are freely and uniformly branching with numerous large inflorescences with dark purplish red-colored ray florets.

The new *Osteospermum* plant originated from a cross-pollination by the Inventor during the winter of 2018 of a proprietary selection of *Osteospermum ecklonis* identified as code number QQ14-091042-006, not patented, as the female, or seed, parent with a proprietary selection of *Osteospermum ecklonis* identified as code number QQ15-067154-002, not patented, as the male, or seed, parent. The new *Osteospermum* plant was discovered and selected by the Inventor as a single flowering plant within the progeny of the stated cross-pollination in a controlled greenhouse environment in De Lier, The Netherlands in July 2020.

Asexual reproduction of the new *Osteospermum* plant by terminal vegetative cuttings in a controlled greenhouse environment in De Lier, The Netherlands since August 2020 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doostmardarpup'. These characteristics in combination distinguish 'Doostmardarpup' as a new and distinct *Osteospermum* plant:

1. Compact, broadly upright, uniform and mounding plant habit.
2. Moderately vigorous growth habit.
3. Freely and uniformly branching habit.
4. Freely and early flowering habit.
5. Large single-type inflorescences with dark purplish red-colored ray florets.

Plants of the new *Osteospermum* differ primarily from plants of the female parent selection in ray floret color as ray florets of plants of the new *Osteospermum* are dark purplish red in color whereas ray florets of plants of the female parent selection are lilac in color. In addition, plants of the new *Osteospermum* have smaller inflorescences than plants of the female parent selection.

Plants of the new *Osteospermum* differ primarily from plants of the male parent selection in ray floret color as ray florets of plants of the new *Osteospermum* are dark purplish red in color whereas ray florets of plants of the male parent selection are lilac in color. In addition, inflorescences of plants of the new *Osteospermum* have more ray florets than inflorescences of plants of the male parent selection.

Plants of the new *Osteospermum* can be compared to plants of the *Osteospermum ecklonis* 'Astra Purple', not patented. In side-by-side comparisons, plants of the new *Osteospermum* differ primarily from plants of 'Astra Purple' in the following characteristics:

1. Plants of the new *Osteospermum* are more compact than plants of 'Astra Purple'.
2. Plants of the new *Osteospermum* are more freely branching than plants of 'Astra Purple'.
3. Plants of the new *Osteospermum* are more freely flowering than plants of 'Astra Purple'.
4. Plants of the new *Osteospermum* have larger inflorescences with more ray florets than plants of 'Astra Purple'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant.

The photograph is a side perspective view of a typical flowering plant of 'Doostmardarpup' grown in a container.

DETAILED BOTANICAL DESCRIPTION

The aforementioned photograph, following observations and measurements describe plants grown during the summer in 19-cm containers in a glass-covered greenhouse in De Lier, The Netherlands and under cultural practices typical of commercial *Osteospermum* production. During the production of the plants, day temperatures ranged from 20° C. to 35° C., night temperatures ranged from 15° C. to 25° C. and 22° C. and light levels were at a minimum 135 watt/$m^2$. Plants were pinched about five weeks after sticking unrooted cuttings; plants were 13 weeks old when the photograph was taken and 18 weeks old when the detailed description was taken. In the following description, color references are made to The Royal Horticultural Society Colour Chart, Fifth Edition, except where general terms of ordinary dictionary significance are used.

Botanical classification: *Osteospermum ecklonis* 'Doostmardarpup'.

Parentage:

*Female, or seed, parent.*—Proprietary selection of *Osteospermum ecklonis* identified as code No. QQ14-091042-006, not patented.

*Male, or pollen, parent.*—Proprietary selection of *Osteospermum ecklonis* identified as code No. QQ15-067154-002, not patented.

Propagation:

*Type.*—Terminal vegetative cuttings.

*Time to initiate roots, summer.*—About 18 days at temperatures about 22° C. to 30° C.

*Time to initiate roots, winter.*—About 21 days at temperatures about 22° C. to 30° C.

*Time to produce a rooted cutting, summer.*—About 25 days at temperatures about 22° C. to 30° C.

*Time to produce a rooted cutting, winter.*—About 28 days at temperatures about 20° C. to 25° C.

*Root description.*—Medium in thickness, fibrous; typically whitish grey in color, actual color of the roots is dependent on substrate composition, water quality, fertilizers, substrate temperature and age of roots.

*Rooting habit.*—Moderately freely branching; medium density.

Plant description:

*Plant form and growth habit.*—Compact, broadly upright, uniform and mounding plant habit; freely branching habit, dense and bushy growth habit; moderately vigorous growth habit and moderate growth rate.

*Plant height, soil level to top of foliar plane.*—About 23 cm.

*Plant height, soil level to top of floral plane.*—About 27 cm.

*Plant diameter.*—About 47 cm.

*Lateral branches.*—Quantity per plant: Freely branching habit, about four primary lateral branches each with about five secondary lateral branches developing per plant; pinching enhances lateral branch development. Length: About 22 cm. Diameter: About 7 mm. Internode length: About 7 mm. Strength: Moderately strong. Texture and luster: Smooth, glabrous; matte. Color, developing and developed: Close to 144B.

*Leaf description.*—Arrangement: Alternate, single. Length: About 7.8 cm. Width: About 3.1 cm. Shape: Lanceolate. Apex: Acute. Base: Cuneate. Margin: Dentate and lobing; sinuses are medium in depth and convergent. Texture and luster, upper and lower surfaces: Smooth, glabrous; semi-glossy. Venation pattern: Pinnate. Color: Developing leaves, upper surface: Close to 137B. Developing leaves, lower surface: Close to 137C. Fully expanded leaves, upper surface: Close to 137B; venation, close to 145C. Fully expanded leaves, lower surface: Close to 147B; venation, close to 144C.

*Petioles.*—Length: About 1.6 cm. Diameter: About 5 mm. Texture, upper and lower surfaces: Smooth, glabrous; matte. Strength: Moderately strong. Color, upper and lower surfaces: Close to 144C.

Inflorescence description:

*Appearance and aspect.*—Terminal and axillary inflorescences; inflorescences positioned beyond the foliar plane on moderately strong peduncles and face mostly upright to outwardly; single-type inflorescence form with ligulate-shaped ray florets and tubular disc florets; ray and disc florets developing acropetally on a capitulum.

*Flowering habit.*—Freely flowering habit; about 121 inflorescence buds and open inflorescences develop per plant.

*Fragrance.*—Fragrant; typical of *Osteospermums*.

*Flowering response.*—In The Netherlands, plants of the new *Osteospermum* flower continuously from spring until first frost in the autumn; early flowering habit, plants begin flowering about nine weeks after planting rooting cuttings.

*Inflorescence longevity.*—Inflorescences last about two weeks on the plant; inflorescences persistent.

*Inflorescence buds.*—Height: About 1.7 cm. Diameter: About 1.1 cm. Shape: Ovoid. Texture and luster: Smooth, glabrous; matte. Color: Close to 143C.

*Inflorescence size.*—Diameter: About 5 cm. Depth (height): About 2 cm. Disc diameter: About 1 cm. Receptacle diameter: About 8 mm to 12 mm. Receptacle height: About 2 mm to 3 mm. Receptacle color: Close to 144A.

*Ray florets.*—Quantity per inflorescence and arrangement: About 24arranged in one to two whorls. Length: About 2.5 cm. Width: About 8 mm. Shape: Ligulate. Apex: Acute or retuse. Base: Cuneate. Margin: Entire; not undulate. Aspect: Mostly flat. Texture and luster, upper and lower surfaces: Smooth, glabrous; semi-glossy. Color: When opening, upper surface: Close to N81A. When opening, lower surface: Close to N77B. Fully opened, upper surface: Close to N79C; venation, close to N79B; color does not change with subsequent development. Fully opened, lower surface: Close to N77B; venation, close to N77A; color does not change with subsequent development.

*Disc florets.*—Quantity per inflorescence and arrangement: About 40arranged in about four to five whorls. Length: About 5 mm. Diameter: About 2 mm. Shape: Tubular with obtuse apices. Aspect: Upright. Texture and luster, inner and outer surfaces: Smooth, glabrous; glossy. Color: When developing, inner and outer surfaces: Close to 9A. Fully developed, inner and outer surfaces: Close to 9A.

*Phyllaries.*—Quantity per inflorescence and arrangement: About 20 arranged in one to two whorls. Length: About 1.2 cm. Width: About 2 mm. Shape: Narrowly lanceolate. Apex: Acute. Base: Truncate. Margin: Entire. Texture and luster, upper and lower surfaces: Smooth, glabrous; matte. Color, upper surface: Close to 143A. Color, lower surface: Close to 143C.

*Peduncles.*—Length: About 5.5 cm. Diameter: About 2 mm. Strength: Moderately strong. Aspect: Mostly upright to outwardly slanting. Texture and luster: Pubescent; semi-glossy. Color: Close to 144A; distally, close to N200A.

*Reproductive organs.*—Androecium: Present on disc florets only. Quantity per floret: About five. Filament length: About 7 mm. Filament color: Close to N187A. Anther size: About 1 mm by 3 mm. Anther color: Close to 17A. Pollen amount: Abundant. Pollen color: Close to 17A. Gynoecium: Present on disc florets only. Quantity per floret: One. Pistil length: About 6 mm. Stigma diameter: About 1 mm. Stigma color: Close to 75B. Style length: About 4 mm. Style color: Close to 75B. Ovary color: Close to 75D.

*Fruits and seeds.*—To date, fruit and seed development has not been observed on plants of the new *Osteospermum*.

Pathogen & pest resistance:

To date, plants of the new *Osteospermum* have not been observed to be resistant to pathogens and pests common to *Osteospermum* plants.

Temperature tolerance:

Plants of the new *Osteospermum* have been observed to tolerate temperatures ranging from about 5° C. to about 45° C.

It is claimed:

1. A new and distinct *Osteospermum* plant named 'Doostmardarpup' as herein illustrated and described.

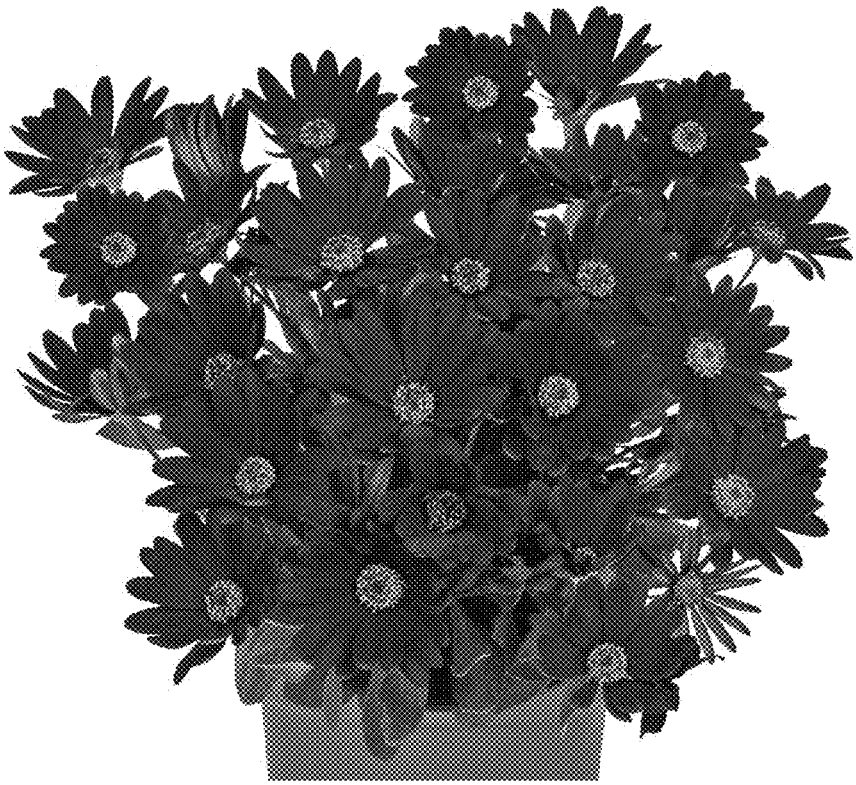

* * * * *